(12) United States Patent
Burke et al.

(10) Patent No.: US 10,455,838 B2
(45) Date of Patent: Oct. 29, 2019

(54) WIPE FOR KILLING SPORES

(71) Applicant: American Sterilizer Company, Mentor, OH (US)

(72) Inventors: Peter A. Burke, Concord, OH (US); Mark James Leggett, Cardiff (GB); Michael A. Centanni, Parma, OH (US)

(73) Assignee: American Sterilizer Company, Mentor, OH (US)

(*) Notice: Subject to any disclaimer, the term of this patent is extended or adjusted under 35 U.S.C. 154(b) by 0 days.

(21) Appl. No.: 15/267,459

(22) Filed: Sep. 16, 2016

(65) Prior Publication Data

US 2017/0000117 A1    Jan. 5, 2017

Related U.S. Application Data

(60) Division of application No. 14/874,940, filed on Oct. 5, 2015, which is a continuation-in-part of application
(Continued)

(51) Int. Cl.
*A01N 37/16* (2006.01)
*A01N 59/00* (2006.01)
(Continued)

(52) U.S. Cl.
CPC ............ *A01N 59/00* (2013.01); *A01N 25/34* (2013.01); *A01N 37/16* (2013.01); *A61K 9/0014* (2013.01); *A61K 9/7007* (2013.01); *A61K 31/327* (2013.01); *A61K 33/40* (2013.01); *A61L 2/186* (2013.01); *B65D 75/30* (2013.01); *B65D 75/5805* (2013.01); *A61L 2/0088* (2013.01);
(Continued)

(58) Field of Classification Search
CPC ........ A01N 37/16; A01N 25/34; A01N 59/00; A61L 2/0088; A61L 2/186; A61L 2/18; A61K 33/40; A61K 45/06; A61K 8/22; A61K 31/327; A61K 9/7007; A61K 9/0014; B65D 75/30; B65D 75/5805
See application file for complete search history.

(56) References Cited

U.S. PATENT DOCUMENTS 3,786,615 A    1/1974   Bauer
4,051,058 A    9/1977   Bowing
(Continued)

FOREIGN PATENT DOCUMENTS

EP    1252819        10/2002
EP    1293215 A1     3/2003
(Continued)

OTHER PUBLICATIONS

International Search Report and Written Opinion, Application No. PCT/US2015/015091, dated Apr. 30, 2015.
(Continued)

*Primary Examiner* — Regina M Yoo
(74) *Attorney, Agent, or Firm* — Renner, Otto, Boisselle & Sklar, LLP

(57) ABSTRACT

This invention relates to a wipe for killing spores comprising an absorbent sheet holding an aqueous composition and a sealed package containing the absorbent sheet, wherein the aqueous composition comprises water, an antimicrobial agent and a peroxide. The invention also relates to a process for killing spores using the above-indicated wipe.

10 Claims, 2 Drawing Sheets

Related U.S. Application Data

No. 14/537,958, filed on Nov. 11, 2014, and a continuation-in-part of application No. 14/538,011, filed on Nov. 11, 2014, and a continuation-in-part of application No. 14/525,497, filed on Oct. 28, 2014, and a continuation-in-part of application No. 14/262,840, filed on Apr. 28, 2014, said application No. 14/525,497 is a continuation-in-part of application No. 14/262,840, filed on Apr. 28, 2014, said application No. 14/538,011 is a continuation-in-part of application No. 14/525,497, filed on Oct. 28, 2014, said application No. 14/537,958 is a continuation-in-part of application No. 14/525,497, filed on Oct. 28, 2014.

(51) Int. Cl.

| | | |
|---|---|---|
| *A01N 25/34* | (2006.01) | |
| *A61K 9/70* | (2006.01) | |
| *A61K 31/327* | (2006.01) | |
| *A61K 9/00* | (2006.01) | |
| *B65D 75/30* | (2006.01) | |
| *B65D 75/58* | (2006.01) | |
| *A61K 33/40* | (2006.01) | |
| *A61L 2/18* | (2006.01) | |
| *A61L 2/00* | (2006.01) | |

(52) U.S. Cl.
CPC ....... *A61L 2202/21* (2013.01); *A61L 2202/24* (2013.01)

(56) References Cited

U.S. PATENT DOCUMENTS

| | | |
|---|---|---|
| 4,051,059 A | 9/1977 | Bowing |
| 4,269,602 A | 5/1981 | Worth |
| 4,731,222 A | 3/1988 | Kralovic et al. |
| 4,743,447 A | 5/1988 | Le Rouzic |
| 4,749,080 A | 6/1988 | Toohey |
| 4,892,706 A | 1/1990 | Kralovic et al. |
| 4,896,768 A | 1/1990 | Anderson |
| 4,910,014 A | 3/1990 | Nakagawa |
| 4,998,984 A | 3/1991 | McClendon |
| 5,190,724 A | 3/1993 | Hachmann |
| 5,437,868 A | 8/1995 | Oakes |
| 5,508,046 A | 4/1996 | Cosentino et al. |
| 5,527,508 A | 6/1996 | Childers et al. |
| 5,656,302 A | 8/1997 | Cosentino |
| 5,753,246 A | 5/1998 | Peters |
| 5,767,163 A | 6/1998 | Kundsin |
| 5,770,232 A | 6/1998 | Sizer |
| 5,851,483 A * | 12/1998 | Nicolle .................. A01N 59/00 422/28 |
| 5,900,256 A | 5/1999 | Scoville, Jr. et al. |
| 6,082,534 A | 7/2000 | Dotson |
| 6,168,808 B1 | 1/2001 | Golden et al. |
| 6,224,827 B1 | 5/2001 | Lembke |
| 6,305,531 B1 | 10/2001 | Wilkman |
| 6,313,049 B1 | 11/2001 | Heady et al. |
| 6,326,032 B1 | 12/2001 | Richter |
| 6,346,279 B1 | 2/2002 | Rochon |
| 6,446,795 B1 | 9/2002 | Allen et al. |
| 6,448,062 B1 | 9/2002 | Huth |
| 6,589,565 B1 | 7/2003 | Richter |
| 6,686,324 B2 | 2/2004 | Ramirez et al. |
| 6,734,405 B2 | 5/2004 | Centanni et al. |
| 6,803,057 B2 | 10/2004 | Ramirez et al. |
| 6,906,296 B2 | 6/2005 | Centanni et al. |
| 6,967,315 B2 | 11/2005 | Centanni et al. |
| 7,135,142 B2 | 11/2006 | Burke et al. |
| 7,300,638 B2 | 11/2007 | Williams et al. |
| 7,354,604 B2 | 4/2008 | Ramirez et al. |
| 7,435,303 B2 | 10/2008 | Biering |
| 7,569,182 B2 | 8/2009 | Burke et al. |
| 7,632,523 B2 | 12/2009 | Ramirez et al. |
| 7,655,252 B2 | 2/2010 | Baker, Jr. |
| 7,781,388 B2 | 8/2010 | Heintz |
| 7,985,773 B2 | 7/2011 | Greten et al. |
| 8,143,309 B2 | 3/2012 | Awad |
| 8,470,755 B1 | 6/2013 | Tajmamet |
| 2001/0001479 A1 | 5/2001 | Johnson |
| 2003/0096720 A1 | 5/2003 | Huth et al. |
| 2003/0099717 A1 | 5/2003 | Cabrera |
| 2003/0180377 A1 | 9/2003 | Ramirez et al. |
| 2004/0022867 A1 | 2/2004 | Tucker et al. |
| 2004/0047915 A1 | 3/2004 | Day |
| 2005/0084415 A1 | 4/2005 | McVey et al. |
| 2005/0095168 A1 | 5/2005 | Centanni et al. |
| 2005/0151117 A1 * | 7/2005 | Man .................. A01N 37/16 252/186.1 |
| 2005/0161636 A1 * | 7/2005 | Man .................. A01N 37/16 252/186.1 |
| 2006/0157495 A1 | 7/2006 | Reddy et al. |
| 2006/0193816 A1 * | 8/2006 | Elfersy .................. A01N 33/12 424/70.28 |
| 2006/0204467 A1 | 9/2006 | Littau |
| 2006/0229225 A1 | 10/2006 | Martin et al. |
| 2006/0292031 A1 | 12/2006 | Chiu |
| 2007/0053850 A1 | 3/2007 | Tichy et al. |
| 2007/0264356 A1 * | 11/2007 | Ames .................. A61L 2/186 424/616 |
| 2008/0045593 A1 | 2/2008 | Kaiser et al. |
| 2008/0240978 A1 | 10/2008 | Sorensen |
| 2008/0305183 A1 * | 12/2008 | Croud .................. A01N 59/00 424/616 |
| 2009/0061017 A1 | 3/2009 | Pedersen et al. |
| 2009/0074881 A1 | 3/2009 | Kielbania, Jr. |
| 2009/0252775 A1 | 10/2009 | Arndt et al. |
| 2010/0189599 A1 | 7/2010 | Bobbert |
| 2010/0284855 A1 | 11/2010 | Erickson |
| 2011/0076192 A1 | 3/2011 | Robitaille et al. |
| 2011/0217204 A1 * | 9/2011 | Franciskovich ....... A01N 37/16 422/29 |
| 2012/0171300 A1 | 7/2012 | Koenig et al. |
| 2012/0174872 A1 | 7/2012 | Richards |
| 2012/0189494 A1 | 7/2012 | Rovison, Jr. et al. |
| 2012/0230870 A1 | 9/2012 | Franciskovich et al. |
| 2013/0251590 A1 * | 9/2013 | Golden .................. A01N 59/00 422/24 |
| 2014/0004208 A1 * | 1/2014 | Golden .................. A01N 59/00 424/616 |
| 2014/0037499 A1 | 2/2014 | Shannon et al. |
| 2015/0314025 A1 | 11/2015 | Berentsveig et al. |
| 2016/0199322 A1 * | 7/2016 | Myntti .................. A01N 25/02 514/643 |

FOREIGN PATENT DOCUMENTS

| | | |
|---|---|---|
| JP | 7-126109 | 5/1995 |
| JP | 2001199811 A1 | 7/2001 |
| WO | 8808667 | 11/1988 |
| WO | 2004020562 | 3/2004 |
| WO | 2008111893 | 9/2008 |
| WO | 2012075507 | 6/2012 |
| WO | WO 2012075507 A2 | 6/2012 |
| WO | WO 2013037014 A1 | 3/2013 |

OTHER PUBLICATIONS

U.S. Appl. No. 14/262,840, filed Apr. 28, 2014.
U.S. Appl. No. 14/525,497, filed Oct. 28, 2014.
U.S. Appl. No. 14/538,011, filed Nov. 11, 2014.
Alasri et al., Canadian Journal of Microbiology 1993 (39):52-60.
Khadre et al.; "Sporicidal action of ozone and hydrogen peroxide: a comparative study"; International Journal of Food Microbiology 71 (2001); pp. 131-138.
"Guideline for Disinfection and Sterilization in Healthcare Facilities, 2008"; Centers for Disease Control and Prevention; CDC—Disinfection & Sterilization Guideline: Disinfection—HICPAC; http://www.cdc.gov/hicpac/disinfection_sterilization/6; 6 pages, Nov. 2008.

(56) References Cited

OTHER PUBLICATIONS

STERIS® Product Brochure; SPOR-KLENZ® Ready to Use; Dec. 1, 2001; 3 pages.
MINNTECH Renal Systems; Actril® Cold Sterilant Product Brochure; Technical Notes and Research Data; Oct. 1, 1998; 12 pages.
Ecolab; Oxonia Active Product Brochure; 2003; 2 pages.
U.S. Appl. No. 14/537,958, filed Nov. 11, 2014.
International Search Report and Written Opinion, Application No. PCT/US2015/015088, dated May 6, 2015.
International Search Report and Written Opinion, Application No. PCT/US2015/015087, dated Apr. 30, 2015.
International Search Report and Written Opinion, Application No. PCT/US2015/015090, dated May 8, 2015.
Leggett et al.; "Resistance to and killing by the sporicidal microbicide peracetic acid"; Journal of Antimicrobial Chemotherapy; Nov. 26, 2014.
Product Brochure; CeBeR™ Multi-Purpose Wipes; STERIS Corporation, 2014.
CeBeR Multi Purpose Wipes (CeBeR MPW); STERIS; http://www.steris.com/products/viewDef.cfm?id+5087, 2015.
American Chemical Society; "New Wipes' for Better Decontamination of Chemical Warfare Agents and Toxic Chemicals"; Science Daily; Dec. 9, 2008; http://www.sciencedaily.com/releases/2008/12/081208081002.htm.

* cited by examiner

WIPE FOR KILLING SPORES

This application is a division of U.S. application Ser. No. 14/874,940, filed Oct. 5, 2015. U.S. application Ser. No. 14/874,940 is a continuation-in-part of U.S. application Ser. No. 14/262,840, filed Apr. 28, 2014. U.S. application Ser. No. 14/874,940 is also a continuation-in-part of U.S. application Ser. No. 14/525,497, filed Oct. 28, 2014, which is a continuation-in-part of U.S. application Ser. No. 14/262,840, filed Apr. 28, 2014. U.S. application Ser. No. 14/874,940 is also a continuation-in-part of U.S. application Ser. No. 14/525,497, filed Oct. 28, 2014, which is a continuation-in-part of U.S. application Ser. No. 14/262,840, filed Apr. 28, 2014. U.S. application Ser. No. 14/874,940 is also a continuation-in-part of U.S. application Ser. No. 14/538,011, filed Nov. 11, 2014, which is a continuation-in-part of U.S. application Ser. No. 14/525,497, filed Oct. 28, 2014, which is a continuation-in-part of U.S. application Ser. No. 14/262,840, filed Apr. 28, 2014. U.S. application Ser. No. 14/874,940 is also a continuation-in-part of U.S. application Ser. No. 14/537,958, filed Nov. 11, 2014, which is a continuation-in-part of U.S. application Ser. No. 14/525,497, filed Oct. 28, 2014, which is a continuation-in-part of U.S. application Ser. No. 14/262,840, filed Apr. 28, 2014. These prior applications are incorporated herein by reference.

TECHNICAL FIELD

This invention relates to wipes for killing spores, and more particularly, to a wipe comprising an absorbent sheet holding an aqueous composition, and a sealed package containing the absorbent sheet, wherein the aqueous composition contains an antimicrobial agent (e.g., peracetic acid) and a peroxide (e.g., hydrogen peroxide).

BACKGROUND

Spores are a highly resistant, dormant cell type formed by some types of bacteria. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault. Spore forming bacteria cause a number of serious diseases in humans, including botulism, gas gangrene, tetanus, and acute food poisoning. Anthrax results from infection by the aerobic spore form *Bacillus anthracis*.

SUMMARY

Spores are difficult to kill and a problem in the art of sterilization relates to providing effective wipes for killing spores. This invention provides a solution to this problem. This invention relates to a wipe for killing spores comprising an absorbent sheet holding an aqueous composition, and a sealed package containing the absorbent sheet. The aqueous composition may comprise water, an antimicrobial agent (e.g., peracetic acid) and a peroxide (e.g., hydrogen peroxide). The concentration of the peroxide may be in the range from about 0.01 to about 14% by weight, or from about 0.1 to about 6.5% by weight. The concentration of the antimicrobial agent is in the range from about 0.001 to about 5% by weight, or from about 0.001 to about 0.075% by weight. The weight ratio of the antimicrobial agent to the peroxide may be in the range from about 0.001 to about 0.5, or from about 0.003 to about 0.4, or from about 0.006 to about 0.3, or from about 0.008 to about 0.2, or from about 0.01 to about 0.1. In an embodiment, the aqueous composition may comprise water, peracetic acid and hydrogen peroxide, the concentration of peracetic acid in the water may be in the range from about 0.005 to about 0.075% by weight; the concentration of the hydrogen peroxide in the water may be in the range from about 0.1 to about 6.5% by weight; and the weight ratio of peracetic acid to hydrogen peroxide may be in the range from about 0.001 to about 0.5.

The above-indicated wipe may be used in a process for killing spores positioned on a substrate. The process may comprise wiping the spores from the substrate using the absorbent sheet holding the aqueous composition and contacting the spores with the aqueous composition held by the absorbent sheet; and maintaining the aqueous composition in contact with the spores for an effective period of time to effect at least a 4 log reduction, or at least a 5 log reduction, or at least a 6 log reduction in the number of spores capable of returning to vegetative growth. The effective period of time may be in the range from about 30 seconds to about 20 minutes, or from about 30 seconds to about 10 minutes.

BRIEF DESCRIPTION OF THE DRAWINGS

In the annexed drawings, like parts and features have like designations.

DETAILED DESCRIPTION

Figure 1:
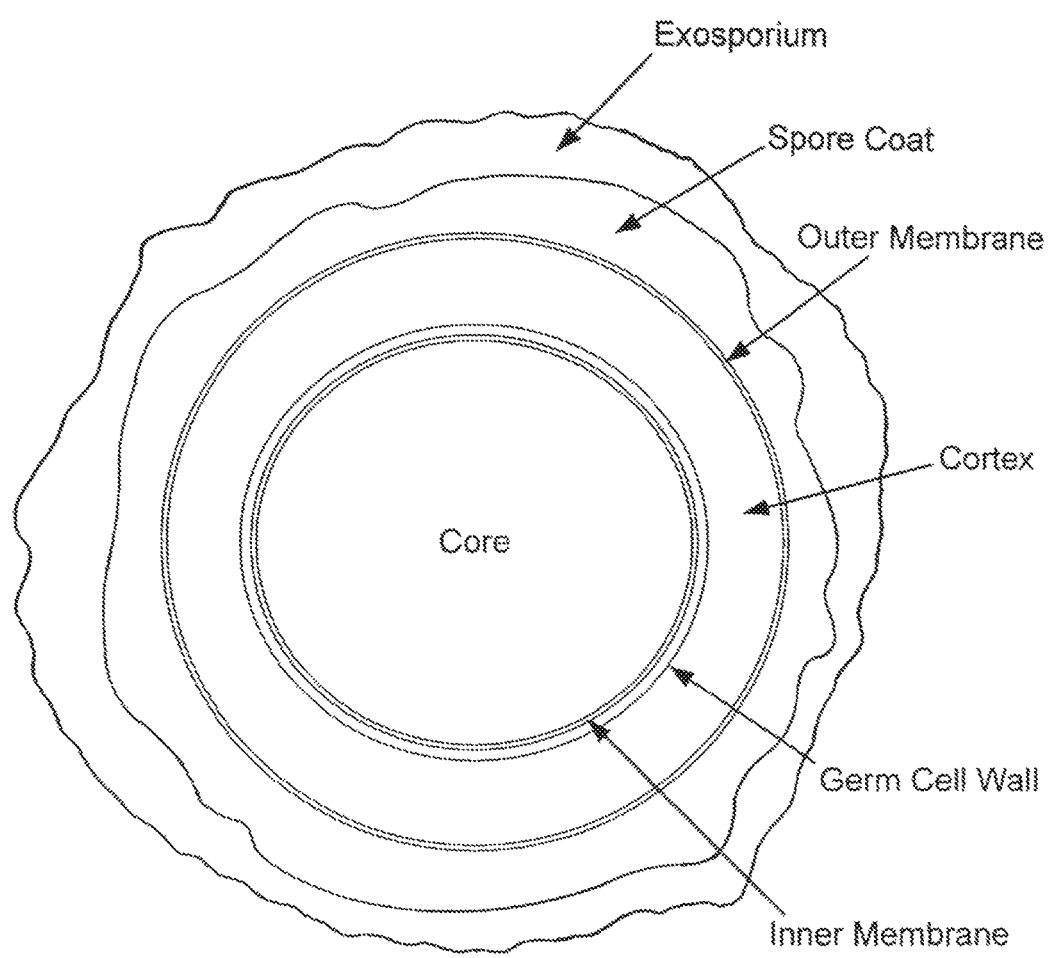
FIG. 1 is a schematic illustration of a spore that can be killed in accordance with the invention.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of"

or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, at least one of A and B" (or, equivalently, "at least one of A or B," or, equivalently at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "killing" (or "kill") spores refers to rendering the spores incapable of returning to vegetative growth. In an embodiment, the term killing spores refers to rendering the spores incapable of reproduction, metabolism and/or growth.

The term "log reduction" is a mathematical term to show the number of live spores killed by contacting the spores with the aqueous composition of the invention. A "4 log reduction" means that the number of live spores is 10,000 times smaller. A "5 log reduction" means that the number of live spores is 100,000 times smaller. A "6 log reduction" means that the number of live spores is 1,000,000 times smaller.

The term "antimicrobial agent" refers to a substance that kills microorganisms or inhibits their growth.

The term "disinfectant" refers to a substance that is applied to non-living objects to kill or inhibit the growth of microorganisms that are on the objects.

The term "antibiotic" refers to a substance that kills or inhibits the growth of microorganisms within the body.

The term "antiseptic" refers to a substance that kills or inhibits the growth of microorganisms on living tissue.

The term "biocide" refers to a substance that kills or inhibits the growth of living organisms. The biocide can be a pesticide. The biocide can be a fungicide, herbicide, insecticide, algaecide, molluscicide, miticide or rodenticide.

The term "sanitizes" refers to a substance that cleans and disinfects.

The term "biodegradable" refers to a material which decomposes upon exposure to air.

Figures 2, 3:
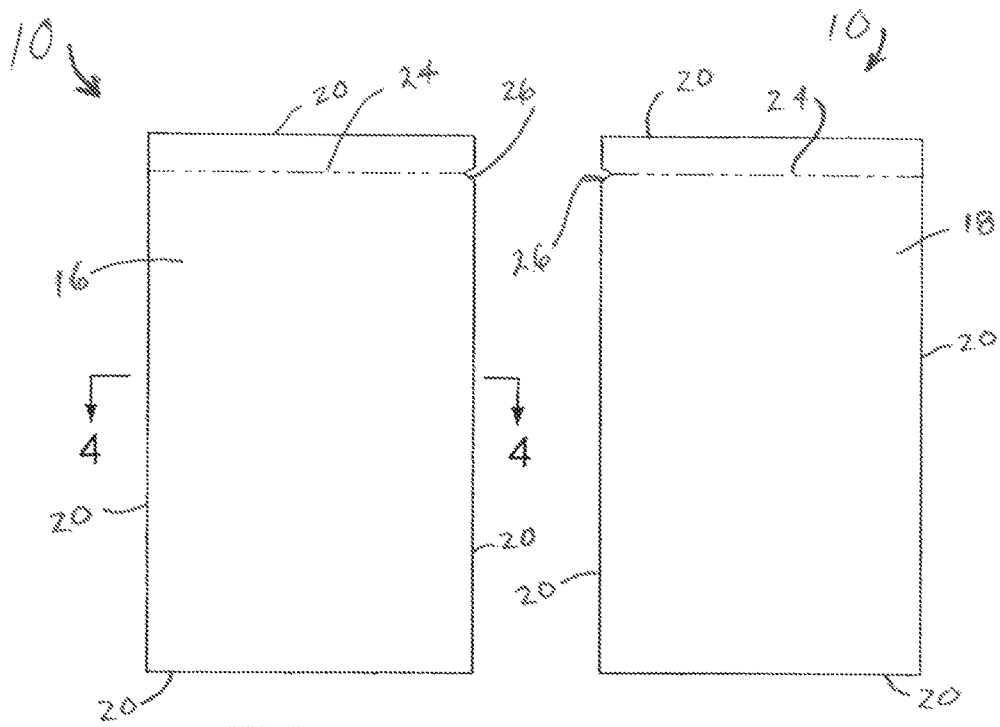
FIG. 2 is a front elevational view of the inventive wipe.
FIG. 3 is a rear elevational view of the inventive wipe.
Figure 4:
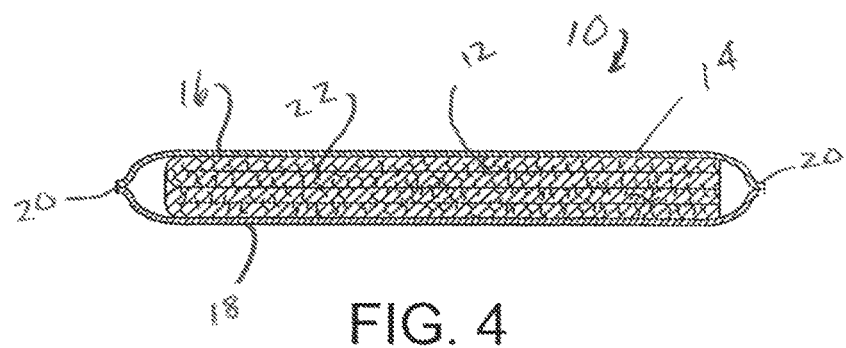
FIG. 4 is a section view in the direction of arrow 4-4 in FIG. 2.

The inventive wipe may be described with reference to FIGS. 2-4. Referring to FIGS. 2-4, wipe 10 comprises absorbent sheet 12 holding the aqueous composition for killing spores. The absorbent sheet 12 with the aqueous composition is contained within sealed package 14. The sealed package 14 has a rectangular shape and is made from non-porous sheets 16 and 18. The non-porous sheets 16 and 18 may be hermetically sealed together along their peripheral edges 20 to form an inner cavity 22 for containing the absorbent sheet 12 and the aqueous composition. The absorbent sheet 12 holding the aqueous composition may be referred to as a saturated absorbent sheet. The sealed package 14 includes tear line 24 and notch 26 which facilitates opening the package 14 along tear line 24. The saturated absorbent sheet 12 may be removed from the sealed package 14 by tearing the sealed package 14 along tear line 24, and then pulling the saturated absorbent sheet 12 out of the torn package.

The absorbent sheet 12 holding the aqueous composition may be referred to as a saturated absorbent sheet. The absorbent sheet may be referred to as a towelette. The absorbent sheet may comprise a wiping pad suitable for wiping a substrate. The absorbent sheet may be made of a material that resists disintegration while in use to effect a suitable wiping of a substrate. The absorbent sheet may be biodegradable. The absorbent sheet may comprise a woven material, a non-woven material, or a combination thereof. The absorbent sheet may comprise natural fibers, synthetic fibers, or a combination thereof. The absorbent sheet may comprise paper, cotton, jute, rayon, polyester, acrylonitrile, nylon, or a combination thereof. The absorbent sheet may comprise a sponge material, polyurethane foam, or a combination thereof. The absorbent sheet may have a surface area in the range from about 5 to about 2000 $cm^2$, or about 10 to about 1500 $cm^2$, or about 20 to about 1000 $cm^2$, or about 50 to about 750 $cm^2$, or about 75 to about 500 $cm^2$, or about 100 to about 250 $cm^2$. The absorbent sheet may have a thickness that is sufficient to absorb and retain the aqueous composition. The absorbent sheet may have a thickness in the range from about 0.01 to about 0.5 cm, or about 0.02 to about 0.4 cm, or about 0.05 to about 0.2 cm. The absorbent sheet may be folded to allow for storage in the sealed package 14.

The sealed package 14 may be square or rectangular in shape. The sealed package may have an air and liquid impermeable construction. The sealed package may have a light impermeable construction. The sealed package may be made of aluminum foil, plastic sheet, coated paper, or a combination thereof. The sealed package may be made of two non-porous sheets with common peripheral edges sealed together. The sealed package may include tear line 24 and notch 26 to facilitate tearing of the sealed package along the tear line. The sealed package may have sufficient dimensions to allow for receiving the absorbent sheet.

The sterilization of spores is often taken as referring to a process for achieving a total absence of living spores. Processes that are less rigorous than sterilization may include, for example, disinfection, sanitization, decontamination, cleaning, and the like. The wipe provided for herein may be used to achieve at least a 4 log reduction, or at least a 5 log reduction, or at least a 6 log reduction in the number of spores capable of returning to vegetative growth, or in an embodiment, capable of reproduction, metabolism and/or growth. When at least a 6 log reduction is achieved, the result may be referred to as a sterilization. When a 4 log reduction or a 5 log reduction is achieved, the result may be considered to be less rigorous than a sterilization, but nevertheless useful for various disinfection, sanitization, decontamination and/or cleaning applications.

Spores typically comprise multiple concentric layers surrounding a central core. This is illustrated in FIG. 1 wherein a bacterial spore is shown which has a central core, inner membrane, germ cell wall, cortex, outer membrane, spore coat and occasionally an exosporium. Oxidizing agents for years have been thought to attack DNA, RNA, protein and most organic matter equally. However, while not wishing to be bound by theory, with the present invention it is believed that the mechanism that is provided involves the peroxide (e.g., hydrogen peroxide) first piercing holes in multiple layers surrounding the central core of the spores, and then the antimicrobial agent advancing through the pierced holes and attacking the central core to kill the spores. This mechanism is believed to occur when using aqueous compositions with relatively low concentrations of the peroxide (e.g., in the range from about 0.01 to about 14% by weight, or from about 0.1 to about 6.5% by weight). This may be particularly so when relatively low concentrations of the antimicrobial agent (e.g., in the range from about 0.001 to about 5% by weight, or from about 0.005 to about 0.075% by weight) are used. In an embodiment, this mechanism is believed to occur when relatively low concentrations of the antimicrobial agent and peroxide are used, as indicated above, and the antimicrobial agent to peroxide weight ratio is relatively low (e.g., in the range from about 0.001 to about 0.5, or about 0.01 to about 0.1). As such, the ratio of antimicrobial agent to peroxide may be considered important with respect to biocidal potentials.

The water may comprise tap water, deionized water, distilled water, water purified by osmosis, or a mixture of two or more thereof.

The peroxide may comprise any compound containing an oxygen-oxygen single bond, or a peroxide group or peroxide ion. Examples include hydrogen peroxide; organic peroxides (e.g., benzoyl peroxide, acetyl acetone peroxide, acetyl benzoyl peroxide, diacetyl peroxide, methyl ethyl ketone peroxide, methyl isobutyl ketone peroxide, acetone peroxide, or a mixture of two or more thereof); peroxy acids (e.g., peroxy carboxylic acid); organic hydroperoxides (e.g., t-butyl hydroperoxide, ethylhydroperoxide, or cumene hydroperoxide); inorganic peroxides such as peroxide salts (e.g., alkali metal or alkaline earth metal peroxides); acid peroxides (e.g., peroxymonosulfuric acid or peroxydisulfuric acid); and mixtures of two or more thereof.

The hydrogen peroxide may be derived from any source of hydrogen peroxide. Hydrogen peroxide is typically available as a solution in water. Hydrogen peroxide concentrations of about 3 to about 8% by weight may be used. Commercial grades of about 30% to about 40% by weight, or about 35% by weight, hydrogen peroxide may be used. Commercial grades of about 70 to about 98% by weight hydrogen peroxide may be used. The higher concentrations would be diluted to provide the desired concentrations of hydrogen peroxide that are indicated above.

The concentration of the peroxide in the water may be in the range from about 0.01 to about 14% by weight, or from about 0.01 to about 12% by weight, or from about 0.01 to about 10% by weight, or from about 0.01 to about 8% by weight, or from about 0.01 to about 7% by weight, or from about 0.05 to about 7% by weight, or from about 0.1 to about 7% by weight, or from about 0.1 to about 6.5% by weight.

The antimicrobial agent may comprise a disinfectant, antibiotic, antiseptic, biocide and/or sanitizer. The antimicrobial agent may comprise peracetic acid. The antimicrobial agent may comprise an alcohol, chlorine, a chlorine compound, an aldehyde, an oxidizing agent, iodine, ozone, a phenolic, a quaternary ammonium compound, or a mixture of two or more thereof. The antimicrobial agent may comprise formaldehyde, ortho-phthalaldehyde, glutaraldehyde, silver dihydrogen citrate, polyaminopropyl biguanide, sodium bicarbonate, lactic acid, chlorine bleach, or a mixture of two or more thereof. The antimicrobial agent may comprise methanol, ethanol, n-propanol, 1-propanol, 2-propanol, isopropanol, or a mixture of two or more thereof. The antimicrobial agent may comprise a hypochlorite, chlorine dioxide, a dichloroisocyanurate, a monochloroisocyanurate, a halogenated hydantoin, or a mixture of two or more thereof. The antimicrobial agent may comprise sodium hypochlorite, calcium hypochlorite, sodium dichloroisocyanurate, sodium chlorite, N-chloro-4-methylbenzenesulfonamide sodium salt, 2,4-dichorobenzyl alcohol, or a mixture of two or more thereof. The antimicrobial agent may comprise performic acid, potassium permanganate, potassium peroxymonosulfate, or a mixture of two or more thereof. The antimicrobial agent may comprise phenol, o-phenylphenol, chloroxylenol, hexachlorophene, thymol, amylmetacresol, or a mixture of two or more thereof. The antimicrobial agent may comprise benzalkonuim chloride, cetyltrimethyl ammonium bromide, cetylpyridinium chloride, benzethonium chloride, boric acid, Brilliant green, chlorhexidine gluconate, tincture of iodine, providone-iodine, mercurochrome, manuka honey, octenidine dihydrochloride, polyhexamethylene biguamide, balsam of Peru, or a mixture of two or more thereof. Many of these antimicrobial agents may not be effective in the killing of spores on their own, but when combined with hydrogen peroxide at the concentration levels indicated above many of these antimicrobial agents are useful for killing spores.

The concentration of the antimicrobial agent in the aqueous composition may be in the range from about 0.001 to about 5% by weight, or from about 0.001 to about 4%, or from about 0.001 to about 3% by weight, or from about 0.001 to about 2% by weight, or from about 0.001 to about 1.5% by weight, or from about 0.001 to about 1% by weight, or from about 0.001 to about 0.8% by weight, or from about 0.001 to about 0.5% by weight, or from about 0.001 to about 0.2% by weight, or from about 0.001 to about 0.18% by weight, or from about 0.001 to about 0.16% by weight, or from about 0.001 to about 0.14% by weight, or from about 0.001 to about 0.12% by weight, or from about 0.001 to about 0.1% by weight, or from about 0.001 to about 0.08% by weight, or from about 0.001 to about 0.075% by weight, or from about 0.001 to about 0.07% by weight, or from about 0.001 to about 0.06% by weight, or from about 0.001 to about 0.05% by weight, or from about 0.001 to about 0.04% by weight. The concentration of the antimicrobial agent may be in the range from about 0.005 to about 0.5% by weight, or from about 0.005 to about 0.4% by weight, or from about 0.005 to about 0.3% by weight, or from about 0.005 to about 0.2% by weight, or from about 0.005 to about 0.18% by weight, or from about 0.005 to about 0.16% by weight, or from about 0.005 to about 0.12% by weight, or from about 0.005 to about 0.1% by weight, or from about 0.005 to about 0.08% by weight, or from about 0.005 to about 0.075% by weight, or from about 0.005 to about 0.07% by weight, or from about 0.005 to about 0.06% by weight, or from about 0.005 to about 0.05% by weight, or from about 0.005 to about 0.04% by weight.

The weight ratio of the antimicrobial agent to peroxide may be in the range from about 0.001 to about 0.5, or from about 0.003 to about 0.4, or from about 0.006 to about 0.3, or from about 0.008 to about 0.2, or from about 0.01 to about 0.1.

The aqueous composition may further comprise acetic acid, sulfuric acid, or a mixture thereof. The concentration of acetic acid may range up to about 60% by weight, or from about 0.001 to about 60% by weight, or from about 0.001 to about 30% by weight, or from about 0.001 to about 10% by weight, or from about 0.001 to about 5% by weight, or from about 0.001 to about 2% by weight. The concentration of sulfuric acid may range up to 3% by weight, or from about 0.001 to about 2% by weight. The concentration of each of these may be in the range up to about 1% by weight, or from about 0.001 to about 1% by weight, or from about 0.001 to about 0.5% by weight, or from about 0.001 to about 0.3% by weight.

The aqueous composition may further comprise one or more surfactants to provide the aqueous composition with surface active properties, one or more buffers to provide buffering capability (pH modulation), one or more corrosion inhibitors to provide corrosion inhibiting properties, and/or one or more chelators to provide chelation capacity (water softening).

The surfactant may comprise any compound that lowers surface tension or provides greater wettability. The surfactant may comprise one or more detergent, wetting agents, emulsifiers, foaming agents and/or dispersants. The surfactant may comprise one or more organic compounds that contain both hydrophobic groups and hydrophilic groups. The surfactant may comprise both a water insoluble component and a water soluble component. The surfactant may comprise one or more anionic, cationic, zwitterionic and/or nonionic compounds. The surfactant may comprise one or more alkanolamines, alkylarylsulfonates, amine oxides, poly(oxyalkylene)s, block copolymers comprising alkylene oxide repeat units, carboxylated alcohol ethoxylates, ethoxylated alcohols, alkyl phenols, ethoxylated alkyl phenols, ethoxylated amines, ethoxylated am ides, oxiranes, ethoxylated fatty acids, ethoxylated fatty esters, ethoxylated oils, fatty esters, fatty acid amides, glycerol esters, glycol esters, sorbitan, sorbitan esters, imidazolines, lecithin, lignin, glycerides (e.g., mono-, di- and/or triglyceride), olefin sulfonates, phosphate esters, ethoxylated and/or propoxylated fatty acids and/or alcohols, sucrose esters, sulfates and/or alcohols and/or ethoxylated alcohols of fatty esters, sulfonates of dodecyl and/or tridecyl benzenes, sulfosuccinates, dodecyl and/or tridecyl benzene sulfonic acids, mixtures of two or more thereof, and the like. The surfactant may comprise ethanolamine, triethanolamine, octyldimethylamine oxide, nonylphenoxy poly(ethyleneoxy)ethanol, polyalkylene glycol, or a mixture of two or more thereof.

The concentration of the surfactant in the aqueous composition may be in the range up to about 10% by weight, or from about 0.5 to about 10% by weight, or from about 0.5 to about 6% by weight, or from about 1 to about 4% by weight.

The buffer may comprise an alkali metal phosphate, an alkali metal carbonate, or a mixture thereof. The alkali metal may comprise sodium or potassium. The buffer may comprise one or more of monosodium phosphate, disodium phosphate, trisodium phosphate, monopotassium phosphate, dipotassium phosphate, tripotassium phosphate, sodium carbonate, or a mixture of two or more thereof. Disodium phosphate may be used. The concentration of the buffer in the aqueous composition may be in the range up to about 50% by weight, or from about 1% by weight to about 50% by weight, or from about 1% by weight to about 40% by weight, or from about 5% by weight to about 40% by weight, or from about 5% by weight to about 35% by weight.

The corrosion inhibitor may comprise benzotriazole, a sodium salt of benzotriazole, tolyltriazole, a sodium salt of tolyltriazole, or a mixture of two or more thereof. Sodium benzotriazole may be used. A commercially available sodium benzotriazole that may be used is available under the trade designation Cobratec 40S which is believed to be a 40% by weight aqueous solution of sodium benzotriazole. The concentration of the corrosion inhibitor in the aqueous composition may be in the range up to about 10% by weight, or from about 0.01% by weight to about 10% by weight, or from about 0.01% by weight to about 5% by weight.

The chelator may comprise ethylenediaminetetraacetic acid, hydroxyethylidenediphosphonic acid, a sodium salt of either of these acids, or a mixture of two or more thereof. A sodium salt of ethylenediaminetetraacetic acid that may be ethylenediaminetetraacetic acid, tetrasodium salt, tetrahydrate. A commercially available ethylenediaminetetraacetic acid, tetrasodium salt, tetrahydrate that may be used may be available from Akzo Nobel under the trade designation Dissolvine 220-S. Dissolvine 220-S is identified by Akzo Nobel as being a chelating agent containing 83-85% by weight ethylenediaminetetraacetic acid, tetrasodium salt, tetrahydrate. The concentration of the chelator in the aqueous composition may be in the range up to about 50% by weight, or from about 0.01% by weight to about 50% by weight, or from about 0.1% by weight to about 30% by weight.

The aqueous composition may further comprise one or more fragrances, dyes, mixtures thereof, and the like.

The inventive process may comprise killing spores positioned on a substrate. This process may comprise wiping the spores from the substrate using the absorbent sheet holding the aqueous composition. The aqueous composition may contact the spores and kill them. The aqueous composition may remain in contact with the spores for an effective period of time to effect a desired level of reduction (e.g., at least a 4 log reduction, or at least a 5 log reduction, or at least a 6 log reduction) in the number of spores capable of returning to vegetative growth, or in an embodiment, capable of reproduction, metabolism and/or growth. The aqueous composition may remain in contact with the spores for about 30 seconds to about 20 minutes, or about 30 seconds to about 10 minutes.

The substrate may be made of any material including brass, copper, aluminum, stainless steel, carbon steel, rubber, plastic, glass, wood, painted surface, or a combination of two or more thereof. The substrate may comprise a table top, counter top, floor, wall, ceiling, window, door, door handle, sink, faucet, toilet, toilet seat, and the like. The substrate may comprise a medical, dental, pharmaceutical, veterinary or mortuary device. The substrate may comprise human skin.

The temperature of the aqueous composition when contacting the spores may be in the range from about 1° C. to about 40° C., or from about 5° C. to about 35° C., or from about 10° C. to about 30° C., or from about 15° C. to about 30° C., or from about 20° C. to about 26° C., or from about 21° C. to about 25° C., or from about 22° C. to about 24° C., or about 22° C., or about 23° C. The temperature may be room temperature.

The spores that may be treated (i.e., killed) include bacterial spores. The spores may comprise bacteria of the *Bacillus* or *Clostridia* genera. The spores may comprise *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans, Bacillus anthracis*, or a mixture of two or more thereof. The spores may comprise one or more *Bacillus subtilis* strains and/or wild type *Bacillus subtilis* spores.

EXAMPLES

The efficacy of the inventive process is assessed using a time kill suspension test method and spores of *Bacillus subtilis*.

Peracetic acid (PAA) and hydrogen peroxide ($H_2O_2$) are prepared as concentrated stocks (3× concentrate). Each test contains 100 μl of the PAA concentrate and 100 μl of the $H_2O_2$ concentrate. Controls containing only PAA or $H_2O_2$ are also prepared. These contain 100 μl of either the PAA concentrate or $H_2O_2$ concentrate and 100 μl of de-ionized water. To each test, 100 μl of spores are added while starting the timer concurrently. The samples are mixed thoroughly. The temperature of the samples is room temperature. At the appropriate contact times, 10 μl of the appropriate test sample are placed into 90 μl of the appropriate neutralizing solution, mixed thoroughly and incubated for at least 10 minutes. Ten fold serial dilutions are prepared through $10^{-6}$ and plated using the drop counting method. The plates are then incubated aerobically at 37° C. for 1-2 days. Following incubation, colony forming units (CFU) are counted using standard plate count techniques and converted to log 10 values for analysis.

The results are indicated in the tables below.

TABLE 1

Time (min) to achieve 4 log reduction for various PAA/$H_2O_2$ combinations (calculated from curves fitted to time/kill data)

| $H_2O_2$ concentration (%) (% by weight) | | | | | | | | |
|---|---|---|---|---|---|---|---|---|
| 6.40 | 48.64 | 15.68 | 7.2 | 7.36 | 3.67 | 2.14 | 1.36 |
| 3.20 | 97.28 | 15.68 | 13.12 | 8.24 | 3.92 | 2.28 | 1.68 |
| 1.60 | 168.96 | 28.16 | 24.32 | 14.08 | 4.64 | 3.52 | 1.82 |
| 0.80 | 343.04 | 33.7 | 32.96 | 19.36 | 7.6 | 3.96 | 1.9 |
| 0.40 | 639.34 | 92.16 | 69.12 | 43.52 | 14.08 | 6.4 | 2.08 |
| 0.20 | 1213.99 | 286.72 | 209.12 | 92.16 | 32 | 11.92 | 2.22 |
| 0.10 | 2305.13 | — | — | 337.92 | 54.4 | 19.36 | 3.28 |
| 0.00 | — | 711625 | 67744.68 | 6449.101 | 613.9362 | 70.40 | 4.64 |
| | 0.00 | 0.005 | 0.01 | 0.02 | 0.04 | 0.08 | 0.16 |
| | PAA concentration (% by weight) | | | | | | |

TABLE 2

PAA kill time divided by PAA/$H_2O_2$ kill time from values in table 1 (i.e. Potentiation of PAA activity in the presence of $H_2O_2$)

| $H_2O_2$ concentration (% by weight) | | | | | | | | |
|---|---|---|---|---|---|---|---|---|
| 6.40 | — | 45384.25 | 9408.98 | 876.24 | 167.29 | 32.90 | 3.41 |
| 3.20 | — | 45384.25 | 5163.47 | 782.66 | 156.62 | 30.88 | 2.76 |
| 1.60 | — | 25270.77 | 2785.55 | 458.03 | 132.31 | 20.00 | 2.55 |
| 0.80 | — | 21116.47 | 2055.36 | 333.11 | 80.78 | 17.78 | 2.44 |
| 0.40 | — | 7721.63 | 980.10 | 148.19 | 43.60 | 11.00 | 2.23 |
| 0.20 | — | 2481.95 | 323.95 | 69.98 | 19.19 | 5.91 | 2.09 |
| 0.10 | — | — | — | 19.08 | 11.29 | 3.64 | 1.41 |
| | 0.00 | 0.005 | 0.01 | 0.02 | 0.04 | 0.08 | 0.16 |
| | PAA concentration (% by weight) | | | | | | |

TABLE 3

$H_2O_2$ kill time divided by PAA/$H_2O_2$ kill time from values in table 1 (i.e. Potentiation of $H_2O_2$ activity in the presence of PAA)

| $H_2O_2$ concentration (% by weight) | | | | | | | | |
|---|---|---|---|---|---|---|---|---|
| 6.40 | — | 3.10 | 6.76 | 6.61 | 13.25 | 22.73 | 35.76 |
| 3.20 | — | 6.20 | 7.41 | 11.81 | 24.82 | 42.67 | 57.90 |
| 1.60 | — | 6.00 | 6.95 | 12.00 | 36.41 | 48.00 | 92.84 |
| 0.80 | — | 10.18 | 10.41 | 17.72 | 45.14 | 86.63 | 180.55 |
| 0.40 | — | 6.94 | 9.25 | 14.69 | 45.41 | 99.90 | 307.38 |
| 0.20 | — | 4.23 | 5.81 | 13.17 | 37.94 | 101.84 | 546.84 |
| 0.10 | — | — | — | 6.82 | 42.37 | 119.07 | 702.78 |
| | 0.00 | 0.005 | 0.01 | 0.02 | 0.04 | 0.08 | 0.16 |
| | PAA concentration (% by weight) | | | | | | |

The values shown in Table 1 represent the time taken (minutes) to achieve a 4 log reduction in spore count in the presence of either PAA or $H_2O_2$ alone, or in combination with each other. For PAA concentrations 0.005, 0.01, 0.02 and 0.04% (in the absence of $H_2O_2$), the values shown are extrapolated based on the experimental data obtained for PAA concentrations 0.08, 0.16 and 0.32%. Similarly, for $H_2O_2$ concentrations 0.1, 0.2 and 0.4% (in the absence of PAA), the values shown are extrapolated from experimental data. All other values are generated from spore kill data.

Table 2 illustrates the potentiation of spore killing by PAA when in the presence of $H_2O_2$. At higher PAA concentrations (0.08 and 0.16% PAA) relatively little activity is gained by the addition of even very high concentrations of $H_2O_2$. For example, 0.16% PAA is only 3.41 times more active in the presence of 6.4% $H_2O_2$, as compared to the activity of 0.16% PAA alone.

However, as the concentration of PAA is reduced, the effect of adding $H_2O_2$ becomes more dramatic, with PAA spore killing activity being hundreds, thousands and even tens of thousands of times greater when in the presence of low concentrations of $H_2O_2$. For example, 0.02% PAA is 333.11 times more active in combination with 0.8% $H_2O_2$ than when used alone.

Table 3 illustrates the potentiation of spore killing by $H_2O_2$ when in the presence of PAA. The enhancement of the spore killing activity of $H_2O_2$ when in the presence of PAA is far less pronounced, with relative improvement in the spore killing activity of $H_2O_2$ in combination with all but the highest concentrations of PAA being no greater than about 100 times.

While the invention has been explained in relation to various embodiments, it is to be understood that modifications thereof may become apparent to those skilled in the art upon reading the specification. Therefore, it is to be understood that the scope of the invention specified herein is intended to include all modifications that may fall within the scope of the appended claims.

The invention claimed is:

1. A process for killing bacterial spores positioned on a substrate, comprising:
   contacting the bacterial spores with an aqueous composition using an absorbent sheet, the aqueous composition consisting essentially of water, peracetic acid, acetic acid, sulfuric acid, and hydrogen peroxide, the concentration of the hydrogen peroxide in the water being in the range from 0.1 to 0.8% by weight, the concentration of the peracetic acid being in the range from 0.005 to 0.08% by weight, the weight ratio of the peracetic acid to the hydrogen peroxide being in the range from 0.001 to 0.1, the concentration of acetic acid being in the range from 0.001 to 0.3% by weight, and the concentration of sulfuric acid being in the range from 0.001 to 0.3% by weight; and
   maintaining the aqueous composition in contact with the bacterial spores at a temperature in the range from about 1° C. to about 40° C. for an effective period of time to effect at least a 4 log reduction in the number of bacterial spores capable of returning to vegetative growth.

2. The process of claim 1 wherein the absorbent substrate is made of a material comprising brass, copper, aluminum, stainless steel, carbon steel, rubber, plastic, glass, wood, painted surface, or a combination of two or more thereof.

3. The process of claim 1 wherein the absorbent substrate comprises a table top, counter top, floor, wall, ceiling, window, door, door handle, sink, faucet, toilet or toilet seat.

4. The process of claim 1 wherein the absorbent substrate comprises a medical, dental, pharmaceutical, veterinary or mortuary device.

5. The process of claim 1 wherein the effective period of time is from about 30 seconds to about 20 minutes.

6. The process of claim 1 wherein the bacterial spores comprise bacteria of the *Bacillus* or *Clostridia* genera.

7. The process of claim 1 wherein the bacterial spores comprise *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans, Bacillus anthracis*, or a mixture of two or more thereof.

8. The process of claim 1 wherein the bacterial spores comprise one or more *Bacillus subtilis* strains.

9. The process of claim 1 wherein the aqueous composition is maintained in contact with the bacterial spores for an effective period of time to effect at least a 5 log reduction in the number of bacterial spores capable of returning to vegetative growth.

10. The process of claim 1 wherein the aqueous composition is maintained in contact with the bacterial spores for an effective period of time to effect at least a 6 log reduction in the number of bacterial spores capable of returning to vegetative growth.

* * * * *